(12) United States Patent
Nakashita et al.

(10) Patent No.: US 12,357,715 B2
(45) Date of Patent: Jul. 15, 2025

(54) INFORMATION PROCESSING APPARATUS AND METHOD OF CONTROLLING INFORMATION PROCESSING APPARATUS

(71) Applicant: CANON KABUSHIKI KAISHA, Tokyo (JP)

(72) Inventors: Tsunahito Nakashita, Chiba (JP); Tsutomu Kubota, Chiba (JP); Motoki Koshigaya, Saitama (JP); Tatsuya Ogawa, Ibaraki (JP); Hidetaka Tabuchi, Chiba (JP)

(73) Assignee: Canon Kabushiki Kaisha, Tokyo (JP)

( * ) Notice: Subject to any disclaimer, the term of this patent is extended or adjusted under 35 U.S.C. 154(b) by 858 days.

(21) Appl. No.: 17/455,174

(22) Filed: Nov. 16, 2021

(65) Prior Publication Data
US 2022/0152238 A1 May 19, 2022

(30) Foreign Application Priority Data
Nov. 19, 2020 (JP) .................... 2020-192830

(51) Int. Cl.
*A61L 2/10* (2006.01)
*A61L 2/24* (2006.01)
*H04N 1/00* (2006.01)

(52) U.S. Cl.
CPC .......... *A61L 2/10* (2013.01); *H04N 1/00503* (2013.01); *H04N 1/00824* (2013.01)

(58) Field of Classification Search
CPC ....................................................... A61L 2/24
See application file for complete search history.

(56) References Cited

U.S. PATENT DOCUMENTS 8,431,910 B1 * 4/2013 Perry .................... A61L 2/10
250/455.11
2021/0338859 A1 * 11/2021 Yu ........................ A61L 2/10

FOREIGN PATENT DOCUMENTS

JP 2006204824 A 8/2006
JP 2014110496 A * 6/2014

OTHER PUBLICATIONS

English Translation of Japanese Document No. JP 2014110496 A provided by ip.com Website: Sato, Akihiro; Image Reader and Image Forming Apparatus; Jun. 12, 2014 (Year: 2014).*

* cited by examiner

*Primary Examiner* — Kevin Joyner
(74) *Attorney, Agent, or Firm* — Canon U.S.A., Inc., IP Division

(57) ABSTRACT

An information processing apparatus including at least one unit that receives a user operation, the information processing apparatus includes an ultraviolet irradiation device that performs disinfection processing for disinfecting at least a part of the at least one unit, an operation unit including a display that provides notification to a user, and a controller, wherein during the disinfection processing for the at least a part of the at least one unit, the controller causes the operation unit to provide notification to the user not to touch the information processing apparatus.

15 Claims, 13 Drawing Sheets

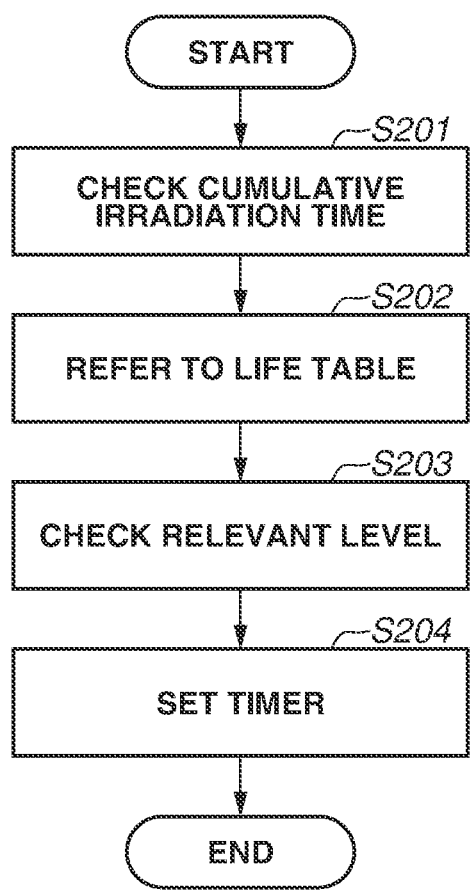

FIG.10

|  | 0 h -- | 1000 h -- | 2000 h -- | 3000 h -- | 10000 h -- | 20000 h -- | 30000 h -- |
|---|---|---|---|---|---|---|---|
| LIGHT SOURCE 200a | 10 sec | 11 sec | 13 sec | 15 sec | -- | -- | -- |
| LIGHT SOURCE 200b | 10 sec | 10 sec | 10 sec | 10 sec | 11 sec | 13 sec | 15 sec |
| LIGHT SOURCE 200c | 10 sec | 10 sec | 10 sec | 10 sec | 11 sec | 13 sec | 15 sec |
| LIGHT SOURCE 200d | 10 sec | 10 sec | 10 sec | 10 sec | 11 sec | 13 sec | 15 sec |

INFORMATION PROCESSING APPARATUS AND METHOD OF CONTROLLING INFORMATION PROCESSING APPARATUS

BACKGROUND

Field

The present disclosure relates to an information processing apparatus and a method of controlling the information processing apparatus.

Description of the Related Art

Image formation apparatuses, such as a copier and a multifunction apparatus, are generally used by the public. Various parts of an image formation apparatus can be touched by various users and/or droplets exhaled by various users can contact the image formation apparatus, the image formation apparatus can be contaminated with, for example, microorganisms such as viruses. Viruses can remain infectious on any glass or plastic surface of an image formation apparatus for several days. Thus, users of the image formation apparatus can spread infections after using the image formation apparatus. The coronavirus disease (COVID-19), which has been widespread since early 2020, is an example of an extremely infectious virus. It has thus recently become even more essential to disinfect publicly shared facilities, machines, etc.

A disinfection method that uses ethanol as a disinfectant is commonly used. However, the disinfection method is not suitable for some parts of image formation apparatuses due to the electric components these apparatuses include. A disinfection method using ultraviolet irradiation is becoming more common. Ultraviolet light source devices for disinfection, especially with wavelengths of 200 to 290 nm, have started to appear in the marketplace.

In disinfection processing using an ultraviolet light source, the amount of light from the light source, a distance from the light source to a disinfection target, an angle between the light source and the disinfection target, and an irradiation time period are important factors. More specifically, the target cannot be sufficiently disinfected unless these aspects are met and integrated illuminance required for disinfection is applied to a target. The integrated illuminance is represented as illuminance (W)×time (seconds), and the unit is J (joules)/cm$^2$. The illuminance represents the intensity of light where the illuminance is inversely proportional to the square of distance to a target with respect to output of the light source and is proportional to the cosine of an incident angle $\theta$.

For example, in an experiment of inactivating norovirus, there is an experimental result indicating that the norovirus level becomes less than or equal to the detection limit by irradiation using an ultraviolet light-emitting diode (LED) with light output of 7 mW at a distance of 10 cm for 30 minutes. According to the result, to disinfect norovirus in a short period of time, e.g., several seconds, using a light source mounted on an image formation apparatus, it is necessary to irradiate a target with ultraviolet rays at an incident angle close to 0 degrees from the shortest possible distance with a high-power ultraviolet light source.

Japanese Patent Application Laid-Open No. 2006-204824 discusses a technique of disinfecting a control panel included in an operation unit, which is frequently used by users, by irradiating the control panel from a front surface or a back side of the control panel with a disinfection lamp after a user has used the control panel.

However, in the above described disinfection processing using ultraviolet rays, mere irradiation of a target with ultraviolet rays is not sufficient, but application of ultraviolet rays with stronger illuminance for a certain period of time is necessary. Since Japanese Patent Application Laid-Open No. 2006-204824 only discusses that the target is directly irradiated using a disinfection lamp, the technique discussed in Japanese Patent Application Laid-Open No. 2006-204824 does not satisfy requirements necessary for disinfection. While the technique of irradiation from the back side of the control panel is also described, since the ultraviolet rays of the disinfection lamp have low transmittance, effective light may not be transmitted by irradiation from the back side. This may result in failure of disinfection.

In a case where an image formation apparatus includes ultraviolet light sources to irradiate respective elements touched by a user, while a disinfection processing time period is determined based on an element to be irradiated and an output level of a corresponding one of the light sources, the disinfection processing is not instantaneous and can take several seconds to several minutes. This can cause a concern for a user touching an element being irradiated during the disinfection processing, which returns the disinfection level to a state before the processing.

SUMMARY

The present disclosure is directed to a technique in which a controller causes an operation unit to notify a user of information for inhibiting a touch on an information processing apparatus while an ultraviolet irradiation device disinfects at least a part of at least one element.

According to an aspect of the present disclosure, an information processing apparatus including at least one unit that receives a user operation, the information processing apparatus includes an ultraviolet irradiation device configured to perform disinfection processing for disinfecting at least a part of the at least one unit, an operation unit including a display that provides notification to a user, and a controller, wherein during the disinfection processing for the at least a part of the at least one unit, the controller causes the operation unit to provide notification to the user not to touch the information processing apparatus.

Further features of the present disclosure will become apparent from the following description of exemplary embodiments with reference to the attached drawings.

BRIEF DESCRIPTION OF THE DRAWINGS

FIG. 9 is a flowchart illustrating setting of a disinfection time period.

FIG. 10 is an irradiation time period setting table.

DESCRIPTION OF THE EMBODIMENTS

Each exemplary embodiment will be described in detail with reference to the attached drawings. In description of each exemplary embodiment, an image formation apparatus will be used as an example of an information processing apparatus. The following exemplary embodiments are not seen to be limiting. Not all combinations of features described in each exemplary embodiment are essential to solutions of the present disclosure.

Figure 1:
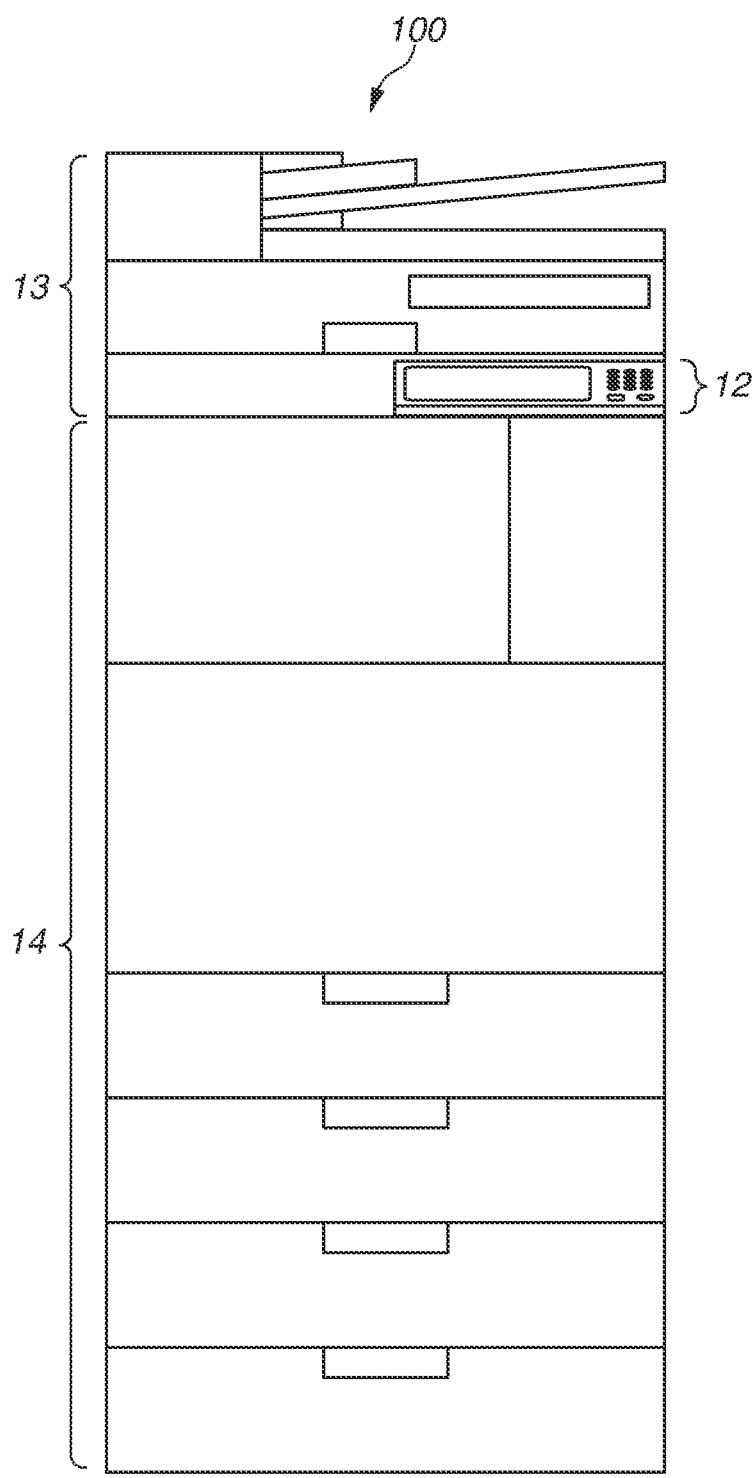
FIG. 1 is a diagram illustrating a front external view of an image formation apparatus.
Figure 2:
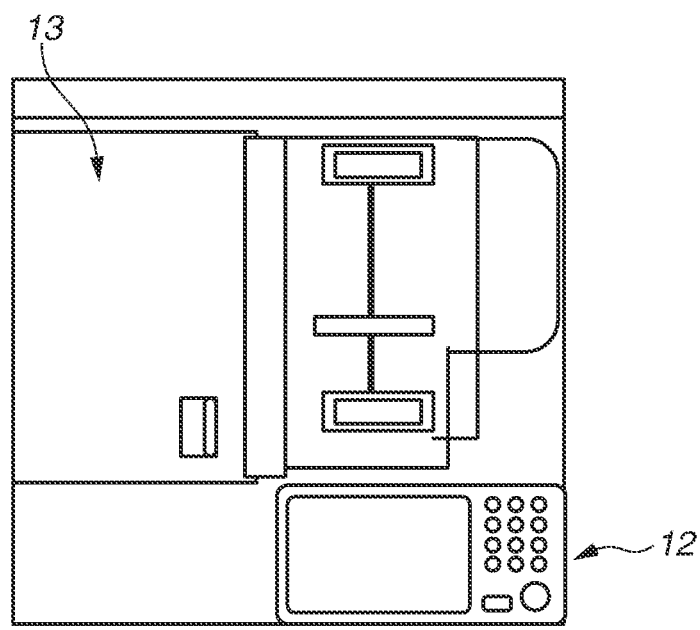
FIG. 2 is a diagram illustrating a top view of the image formation apparatus.

FIGS. 1 and 2 are an external view and a top view, respectively, of an image formation apparatus 100 of a first exemplary embodiment.

The image formation apparatus 100 includes a scanner unit 13 including an automatic document feeder (ADF). The image formation apparatus 100 reads an image of a document and provides image data of the read image to a controller 11 of the image formation apparatus 100. Methods for reading image of a document by the image formation apparatus 100 include reading an image of a document by using the ADF. The methods also include reading an image of a document placed on a document positioning glass (not illustrated) that appears when the ADF is lifted. In the present exemplary embodiment, an operation of lifting and lowering the ADF is referred to as an operation of opening and closing the image formation apparatus 100.

A printer unit 14 includes a laser unit and a photosensitive drum (not illustrated), and prints image data on a sheet. The printed sheet is ejected to a sheet ejection unit (not illustrated). Sheets are stored in sheet feeding cassettes included in the printer unit 14. Sheets are replenished by a user opening a sheet feeding cassette and placing sheets into the sheet feeding cassette.

Figure 3:
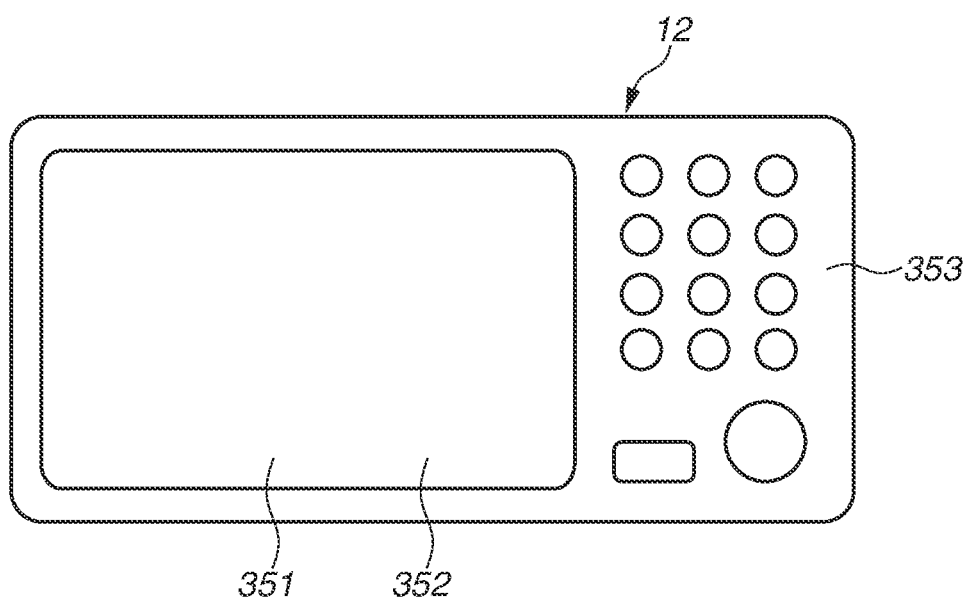
FIG. 3 is a diagram illustrating an external view of an operation unit.

An operation unit 12 includes a liquid crystal display (LCD) 351 and a numeric keypad 353 as illustrated in FIG. 3. The LCD 351 is, for example, a display including a touch panel 352, such as a liquid crystal display and an organic electroluminescence (EL) display, capable of receiving a touch operation by a user. The LCD 351 is used for a user's input operation. By a touch operation of software keys displayed on the LCD 351 or a pressing operation of the numeric keypad 353, various data regarding image formation, a start instruction and an end instruction of the image formation operation, and the like are input into the image formation apparatus 100.

Figure 4:
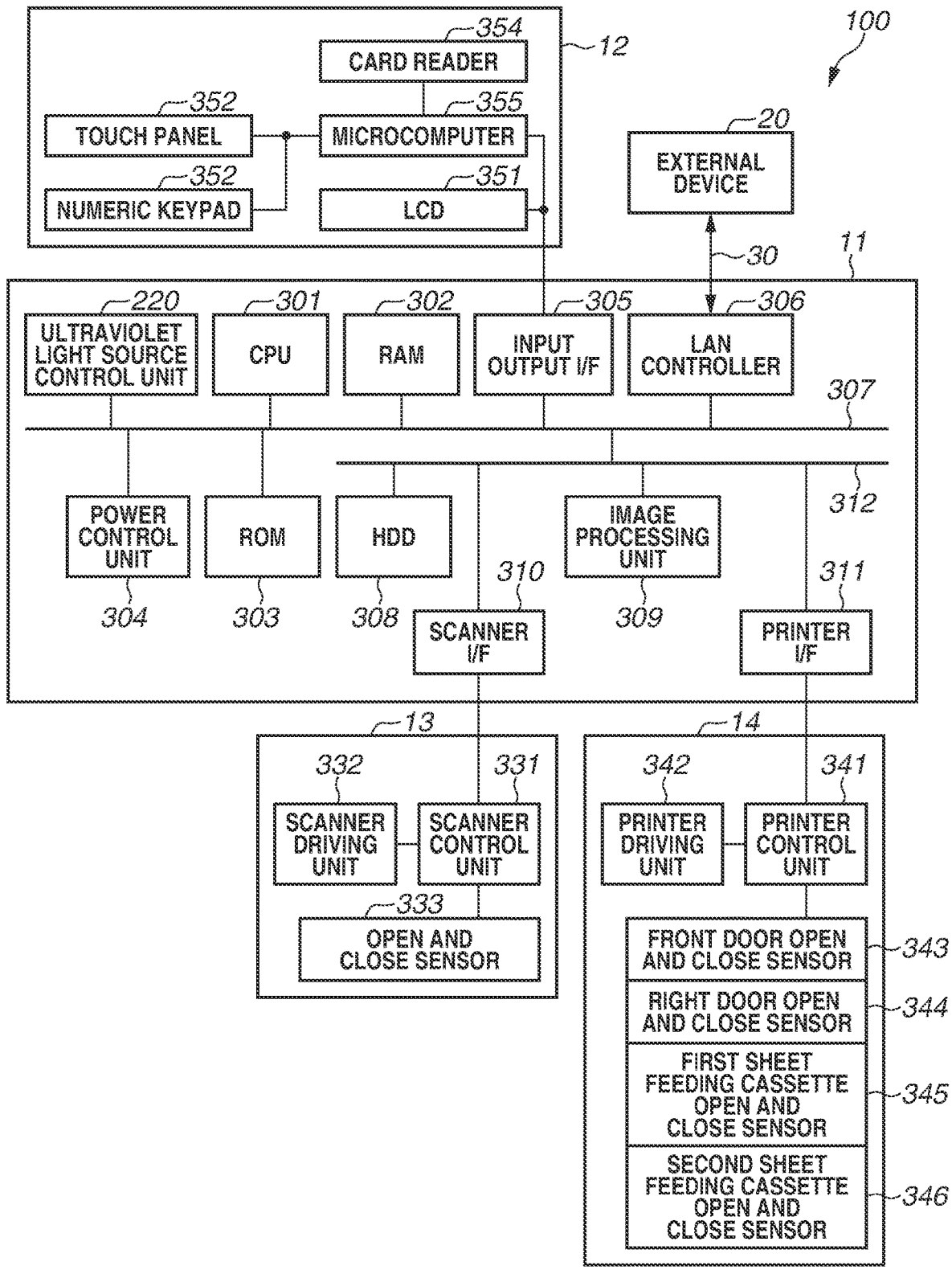
FIG. 4 is a hardware block diagram illustrating the image formation apparatus.

FIG. 4 is a hardware block diagram of the image formation apparatus 100. Details of a controller 11 that controls overall operation of the image formation apparatus 100 will be described with reference to FIG. 4.

As illustrated in FIG. 4, the image formation apparatus 100 includes the controller 11, the operation unit 12, the scanner unit 13, and the printer unit 14.

The controller 11 is connected to the operation unit 12, the scanner unit 13, and the printer unit 14 to enable communication between each of the units. The controller 11 includes a central processing unit (CPU) 301, a random-access memory (RAM) 302, a read-only memory (ROM) 303, a power control unit 304, an input output interface (I/F) 305, and a local area network (LAN) controller 306. The CPU 301, the RAM 302, the ROM 303, the power control unit 304, the input output I/F 305, and the LAN controller 306 are connected to a system bus 307. The controller 11 also includes a hard disk drive (HDD) 308, an image processing unit 309, a scanner I/F 310, and a printer I/F 311. The HDD 308, the image processing unit 309, the scanner I/F 310, and the printer I/F 311 are connected to an image bus 312.

The CPU 301 controls access to various connected elements, based on a control program or the like stored in the ROM 303. The CPU 301 also controls various processing executed by the controller 11. The RAM 302 is a system work memory for operation of the CPU 301. The RAM 302 is also a memory for temporarily storing image data. The ROM 303 stores a boot program for the image formation apparatus 100.

The power control unit 304 controls power supply to each unit of the image formation apparatus 100. Details of the power control unit 304 will be described below. The input output I/F 305 is an interface unit for connecting the system bus 307 to the operation unit 12. The input output I/F 305 receives image data to be displayed on the operation unit 12 from the system bus 307 and outputs the image data to the operation unit 12. The input output I/F 305 also outputs information input from the operation unit 12 to the system bus 307. The LAN controller 306 transmits and receives information to and from an external device 20 connected to a network 30.

The HDD 308 stores system software and image data. The image processing unit 309 performs image processing. The image processing unit 309 reads image data stored in the RAM 302 and performs image processing, such as compression or decompression and color adjustment of the image data having a format of, for example, Joint Photographic Experts Group (JPEG) and Joint Bi-level Image Experts Group (JBIG). The scanner I/F 310 is an interface unit for communicating with a scanner control unit 331 of the scanner unit 13. The printer I/F 311 is an interface unit for communicating with a printer control unit 341 of the printer unit 14. The image bus 312 is a transmission line for exchanging image data and includes a bus, such as a peripheral component interconnect (PCI) bus or a bus in conformity with Institute of Electrical and Electronic Engineers (IEEE) 1394.

The operation unit 12 receives image data transmitted from the CPU 301 via the system bus 307 and displays the image data on the LCD 351. A user input received from the touch panel 352 and the numeric keypad 353 is converted into digital data by a microcomputer 355 and transmitted to the CPU 301 via the system bus 307. When a user inserts an identification (ID) card into a card reader 354, the microcomputer 355 reads data of the ID card and transmits the data to the CPU 301 via the input output I/F 305.

The scanner unit 13 optically reads an image from a document and generates image data. The scanner unit 13 includes the scanner control unit 331, a scanner driving unit 332, and an open and close sensor 333. The scanner driving unit 332 includes a driving unit for moving a reading head for reading a document and a driving unit for conveying a document to a reading position. The scanner control unit 331 controls operations of the scanner driving unit 332. The scanner control unit 331 communicates with the CPU 301 and receives setting information set by the user when performing scanner processing. Based on the setting information, the scanner control unit 331 controls an operation of the scanner driving unit 332. The scanner driving unit 332 has an ADF function for automatically conveying reading document, and the ADF unit can be opened and closed with respect to a glass, which is an image reading surface. The scanner control unit 331 detects the opening and closing of the ADF unit with the open and close sensor 333.

The printer unit 14 forms an image on a recording medium (sheet) by an electrophotographic method. The printer unit 14 includes the printer control unit 341 and a printer driving unit 342. The printer control unit 341 is connected to a front door open and close sensor 343, a right door open and close sensor 344, a first sheet feeding cassette open and close sensor 345 and a second sheet feeding cassette open and close sensor 346, to enable detecting opening and closing of each part of the printer unit 14. The printer driving unit 342 includes a motor for rotating a photosensitive drum, a mechanism for pressurizing a fixing unit, and a heater. The printer control unit 341 controls operations of the printer driving unit 342. The printer control unit 341 communicates with the CPU 301 and receives setting information set by a user when performing print processing. Based on the setting information, the printer control unit 341 controls an operation of the printer driving unit 342.

Figure 5:
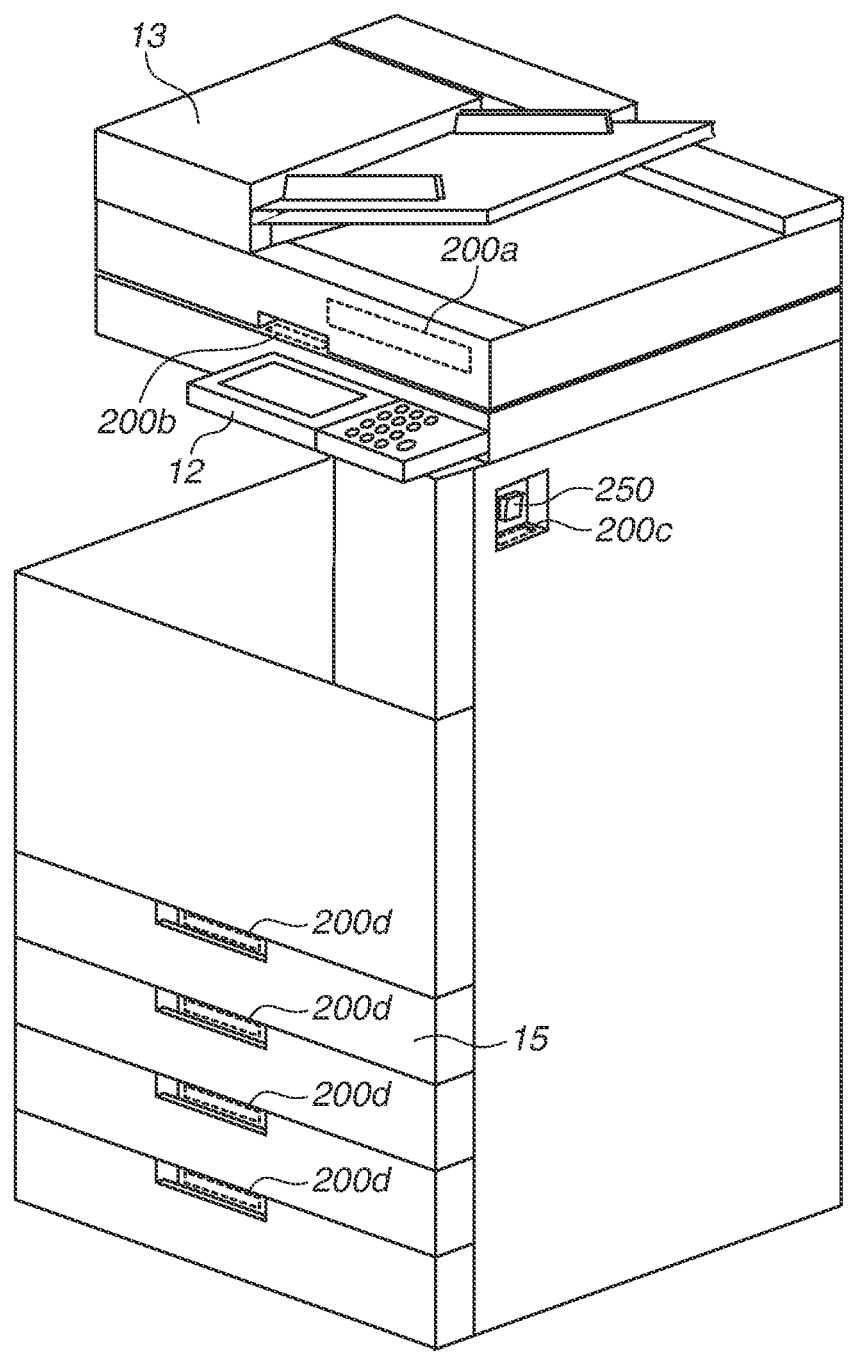
FIG. 5 is a diagram illustrating a perspective view showing layout of ultraviolet light sources.

FIG. 5 is a perspective view illustrating layout of ultraviolet light sources (ultraviolet irradiation devices) in the present exemplary embodiment.

An ultraviolet light source 200a is disposed in the scanner unit 13. To implement an optimized angle between the operation unit 120 and the ultraviolet light source 200a, the ultraviolet light source 200a is disposed at a high position of the scanner unit 13 and is set at an oblique angle to apply irradiation light from the ultraviolet light source 200a to the entire operation unit 12.

An ultraviolet light source 200b is disposed in the scanner unit 13. To perform irradiation from the shortest distance to an operation part (grip part) which is gripped when the user uses the scanner unit 13 and lifts the scanner unit 13, the ultraviolet light source 200b is disposed below the operation part of the scanner unit 13.

An ultraviolet light source 200c is disposed in a recessed part where a power switch 250 is disposed. In a case where the power switch 250 is a seesaw switch (SW), the ultraviolet light source 200c is disposed on both upper and lower side parts of the recessed part to perform irradiation from the shortest distance to a surface of the power switch 250 serving as the operation part, even when the power switch 250 is turned on or off. Based on a switching direction of the power switch 250, the ultraviolet light source 200c can be disposed on both left side and right side parts of the recessed part. In a case where the power switch 250 is a tact SW, the ultraviolet light source 200c is disposed on one side of the upper, lower, left, and right side parts of the recessed part so that the entire power switch 250 is irradiated.

An ultraviolet light source 200d is disposed in a sheet feeding cassette 15. To perform irradiation from the shortest distance to an operation part (grip part) of the sheet feeding cassette 15, which is gripped when a user replenishes the sheet feeding cassette 15 with sheets, the ultraviolet light source 200d is disposed at a back side of the operation part.

Figure 6:
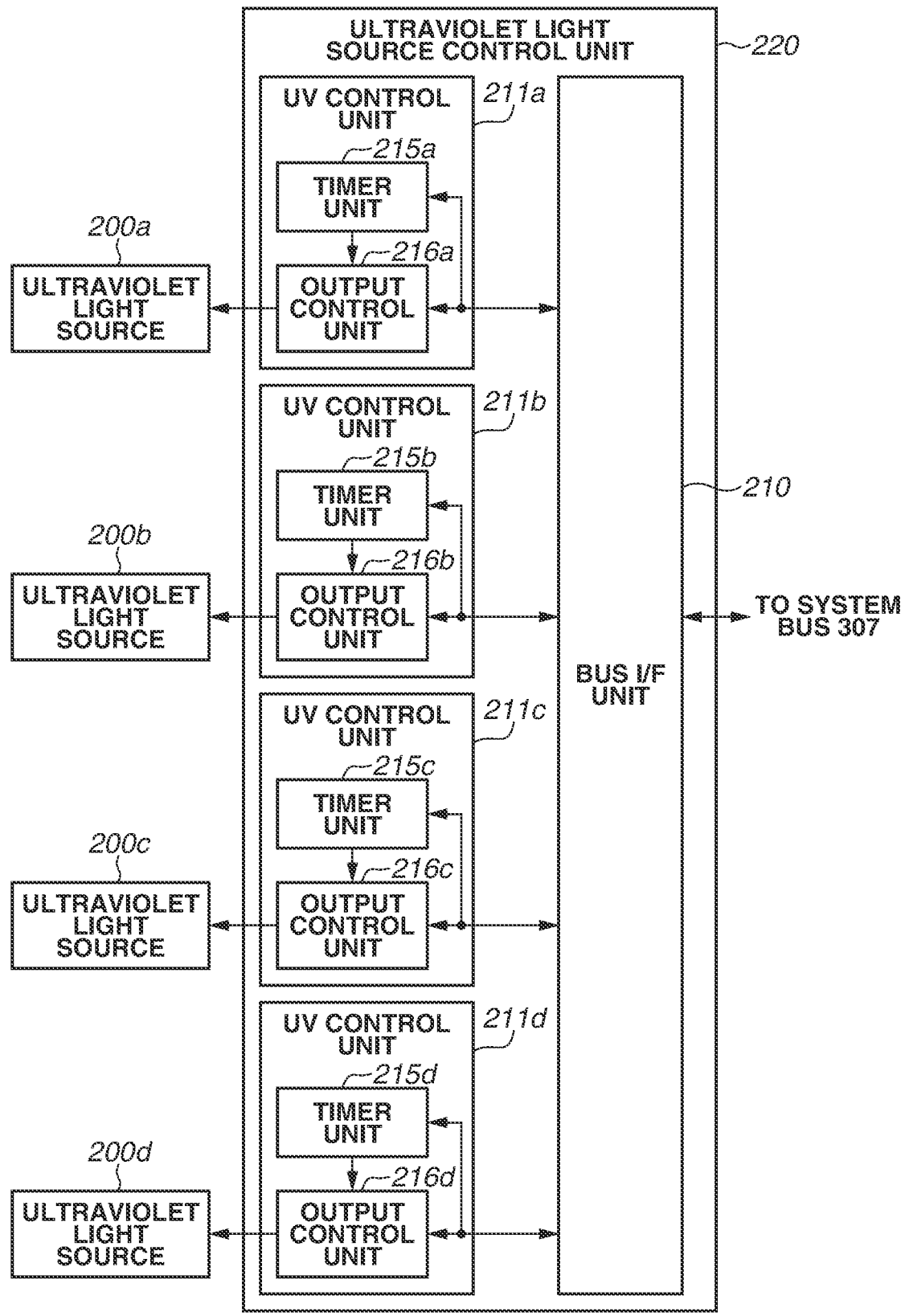
FIG. 6 is a block diagram illustrating an ultraviolet light source control unit.

FIG. 6 is a block diagram of an ultraviolet light source control unit 220 according to the present exemplary embodiment.

The ultraviolet light source control unit 220 includes a bus I/F unit 210 and a plurality of ultraviolet (UV) control units 211 (UV control units 211a to 211d). The ultraviolet light source control unit 220 is controlled by the CPU 301 based on operating states of the switch, the operation unit 12, the scanner unit 13, and the printer unit 14.

The bus I/F unit 210 controls access to the system bus 307. The CPU 301 controls each of the UV control units 211 via the system bus 307 and the bus I/F unit 210.

Each of the UV control units 211 includes a timer unit 215 (timer units 215a to 215d) and an output control unit 216 (output control unit 216a to 216d). In the timer unit 215, a time period for executing disinfection processing is set based on an irradiation output and an installation state of a connected ultraviolet light source and an irradiation target.

The output control unit 216 controls the ultraviolet light source 200 connected to the output control unit 216 to perform irradiation for the time period set by the timer unit 215. In a case where an irradiation output of the connected ultraviolet light source 200 can be adjusted, the CPU 301 controls the irradiation output.

In a case where the operation unit 12 receives an input from the touch panel 352 or the numeric keypad 353, the CPU 301 determines that the user has touched the operation unit 12. The CPU 301 then causes the output control unit 216a to control the ultraviolet light source 200a to perform irradiation for the time period set by the timer unit 215a.

The CPU 301 determines whether the scanner unit 13 has been touched by using the open and close sensor 333 of the scanner unit 13. The CPU 301 then causes the output control unit 216b to control the ultraviolet light source 200b to perform irradiation for the time period set by the timer unit 215b.

The CPU 301 detects off and on of the power switch 250. During startup or shutdown, the CPU 301 causes the output control unit 216c to control the ultraviolet light source 200c to perform irradiation for the time period set by the timer unit 215c.

The CPU 301 determines whether the sheet feeding cassettes have been touched by using the first sheet feeding cassette open and close sensor 345 and the second sheet feeding cassette open and close sensor 346 included in the printer unit 14. The CPU 301 then causes the output control unit 216d to control the ultraviolet light source 200d to perform irradiation for the time period set by the timer unit 215d.

A description will now be provided of a method for inhibiting a user from touching the image formation apparatus 100 during disinfection processing and reliably performing the disinfection processing even in a case where a user touches the image formation apparatus 100.

Figure 7:
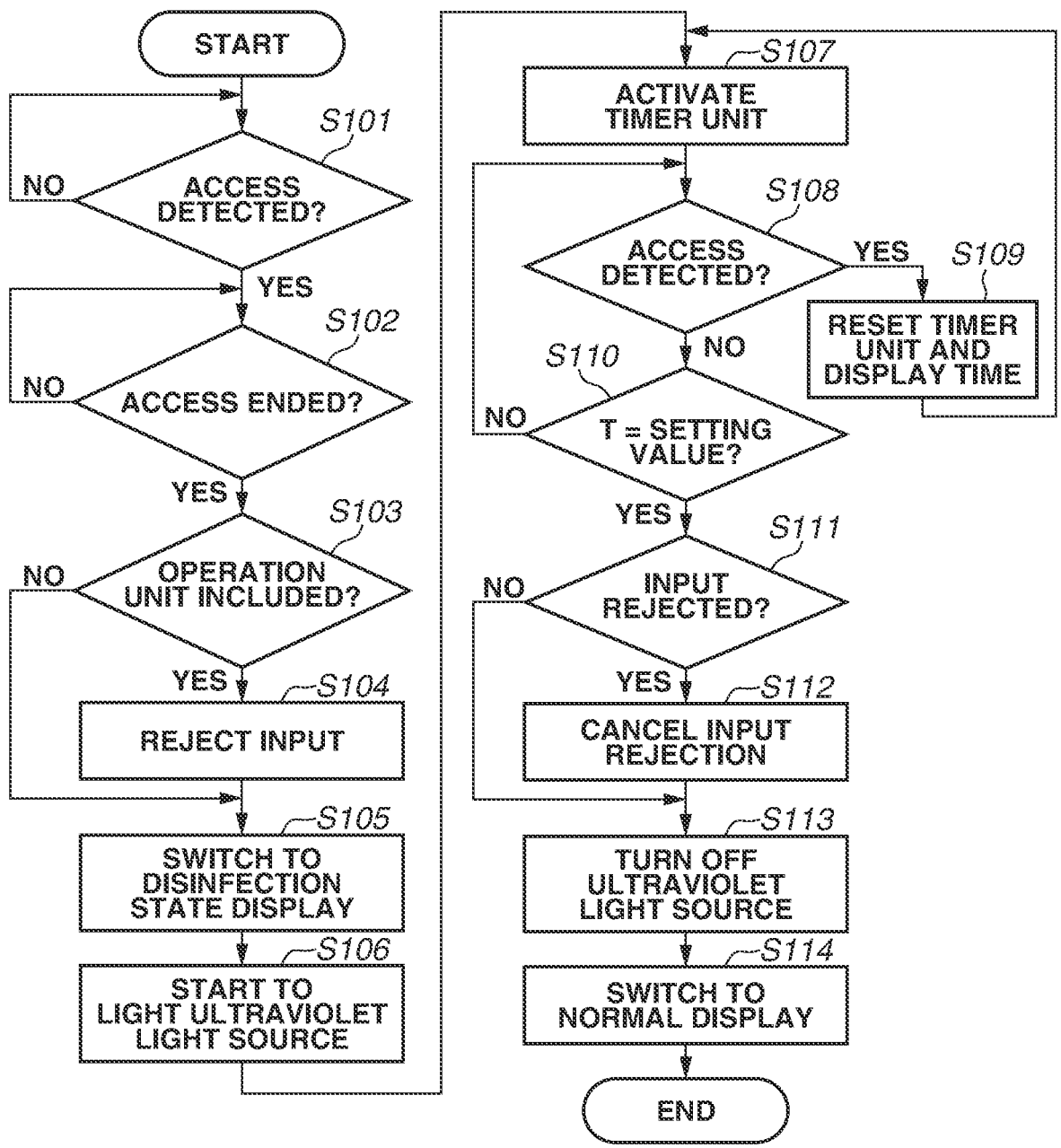
FIG. 7 is a flowchart illustrating disinfection processing.

FIG. 7 is a flowchart illustrating disinfection processing in the present exemplary embodiment.

In step S101, the CPU 301 determines whether a user's access to the image formation apparatus 100, such as an input operation to the operation unit 12, an opening and closing operation of the scanner unit 13, an off and on operation of the power switch 250, or an opening and closing operation of the sheet feeding cassette of the printer unit 14, has been performed.

In a case where detection determination of step S101 is true (YES in step S101), the processing proceeds to step S102, otherwise (NO in step S101) the processing remains in step S101. "True" in the detection determination means detecting opening and closing or off and on of the above-described units.

In step S102, the CPU 301 detects an end of the user's access. In a case where a determination result is true (YES in step S102), the processing proceeds to step S103, otherwise (NO in step S102) the processing remains in step S102. Detection of an end of the access is detecting, for example, a lapse of a predetermined time period since the user has last operated each of the above-described units. In another exemplary embodiment, detection of the end of the access is detecting, for example, a lapse of a predetermined time period since the user last operated the operation unit 12. In another exemplary embodiment, detection of the end of the access is, for example, when the user provides an instruction to shift to a power saving state.

In step S103, in a case where the unit on which the user's access has been detected in steps S101 and S102 includes the operation unit 12 (YES in step S103), the processing proceeds to step S104. In a case where the operation unit 12 is not included (NO in step S103), the processing proceeds to step S105.

In step S104, the CPU 301 deactivates input signals from the touch panel 352 and the numeric keypad 353.

Figure 8A:
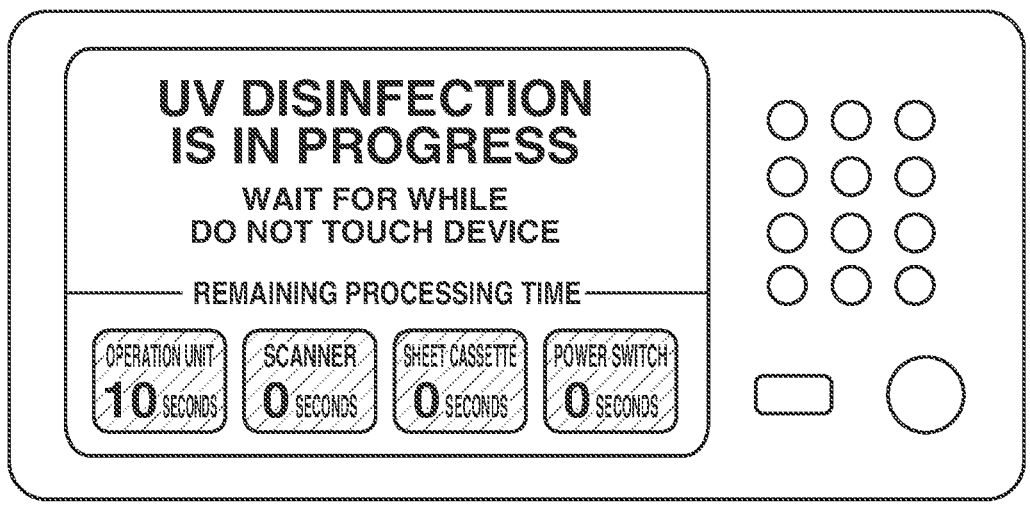
FIGS. 8A and 8B are diagrams each illustrating a display screen of the operation unit.

In step S105, the CPU 301 switches image display of the LCD 351 of the operation unit 12 to a display as illustrated in FIG. 8A. A user is notified that disinfection processing is in progress and that the user needs to wait without touching the image formation apparatus 100 until ultraviolet disinfection ends. The remaining time until the end of disinfection is also displayed.

In step S106, the CPU 301 controls the output control unit 216 to turn on the ultraviolet light source 200 corresponding to the unit on which the user's access has been detected in steps S101 and S102.

In step S107, the CPU 301 activates the timer unit 215 paired with the output control unit 216.

In step S108, the CPU 301 detects whether a user's access to the image formation apparatus 100 is detected. In a case where there is no user access (NO in step S108), the processing proceeds to step S110. In a case where there is a user access (YES in step S108), the processing proceeds to step S109.

In step S109, the CPU 301 resets the timer unit 215 corresponding to the unit on which the user's access is detected, and also resets the remaining time display displayed on the LCD 351 for the disinfection processing of the corresponding unit. The CPU 301 then returns to step S107 to restart the timer unit 215.

In step S110, the CPU 301 checks whether a count value of each of the timer units 215 in operation has reached a setting value set for each of the timer units 215. In a case where the count value reaches the setting value (YES in step S110), the processing proceeds to step S111. In a case where the count value does not reach the setting value (NO in step S110), the processing remains in step S110.

In step S111, in a case where an input operation performed on the touch panel 352 and the numeric keypad 353 is rejected in step S104 (YES in step S111), the processing proceeds to step S112, otherwise (NO in step S111) the processing proceeds to step S113.

In step S112, the CPU 301 cancels rejection of an input from the touch panel 352 and the numeric keypad 353. In step S113, the CPU 301 turns off the ultraviolet light source 200 that has been lit.

Figure 8B:
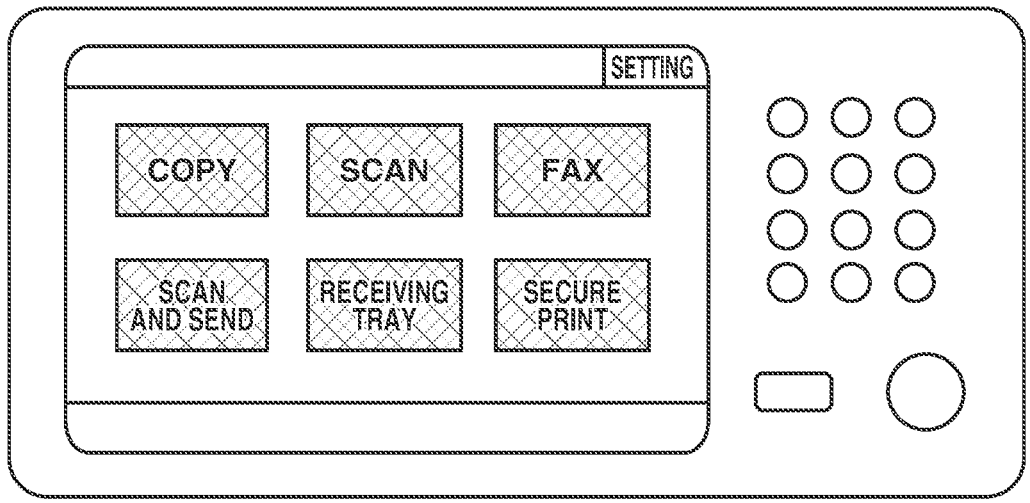

In step S114, the CPU 301 switches display of the LCD 351 of the operation unit 12 to a normal state (standby) display as illustrated in FIG. 8B.

According to the processing of the present exemplary embodiment, the user can be prevented from using the image formation apparatus 100 during the disinfection processing. In addition, the disinfection processing can be reliably performed even in a case where the user touches the image formation apparatus 100.

A description will now be provided of a method for extending the irradiation time period based on a decrease in output of the ultraviolet light source by managing a cumulative irradiation time of the ultraviolet light source. FIG. 9 is a flowchart illustrating setting of the disinfection time period according to a second exemplary embodiment.

In the present exemplary embodiment, a CPU 301 records irradiation time periods one by one for every one of the ultraviolet light sources 200a-200d and stores the recorded time periods in an image formation apparatus 100 as cumulative irradiation time data. A storage destination is, for example, the HDD 308.

A basic processing procedure for the disinfection processing is similar to FIG. 7 of the first exemplary embodiment. In FIG. 9, a disinfection time period during the disinfection processing (steps S106 to S113) of FIG. 7 is set.

In step S201, the CPU 301 checks a cumulative irradiation time of each of the ultraviolet light sources 200a-200d. In step S202, the CPU 301 refers to an output time table as illustrated in FIG. 10 of each of the ultraviolet light sources 200a-200d stored in the image formation apparatus 100. The storage destination of the output time table is, for example, the HDD 308.

Each ultraviolet light source 200a-200d has a different life span depending on a light emitting method. For example, light output of an excimer lamp decreases by 30% from the rated value after 3,000 hours of irradiation. The light output decreases linearly with the irradiation time period. Thus, the light output decreases from the rated value by 10% after 1000-hour irradiation and 20% after 2000-hour irradiation.

FIG. 10 is a table of values of irradiation time period for disinfection each factored in a decrease in an output level of an ultraviolet light source 200a-200d with respect to a different one of cumulative irradiation times.

In step S203, the CPU 301 checks a current level of an irradiation time period of a relevant ultraviolet light source 200a-200d from the cumulative irradiation times of the ultraviolet light source 200a-200d. For example, as illustrated in FIG. 10, in a case of the ultraviolet light source 200a, which has an irradiation time period for disinfection in a new condition of 10 seconds, the required irradiation time period is 11 seconds when the cumulative irradiation time is greater than or equal to 1000 hours and less than 2000 hours because the amount of light will be 90% of the rated value.

In step S204, the CPU 301 sets the value checked in the output time table in step S203 in the timer connected to the ultraviolet light source 200a-200d.

By performing the disinfection processing for the time period in accordance with the output level of each of the ultraviolet light sources 200a-200d based on the processing of the present exemplary embodiment, the integrated illuminance required for the disinfection processing is maintained, and the disinfection processing can be reliably implemented.

A description will now be provided of a method for performing the disinfection processing after detection of a person leaving the vicinity of the image formation apparatus 100, which includes using a human presence sensor (not illustrated) capable of detecting a person in a case where the human presence sensor has detected that a person stays within a predetermined distance from the image formation apparatus 100.

Figure 11:
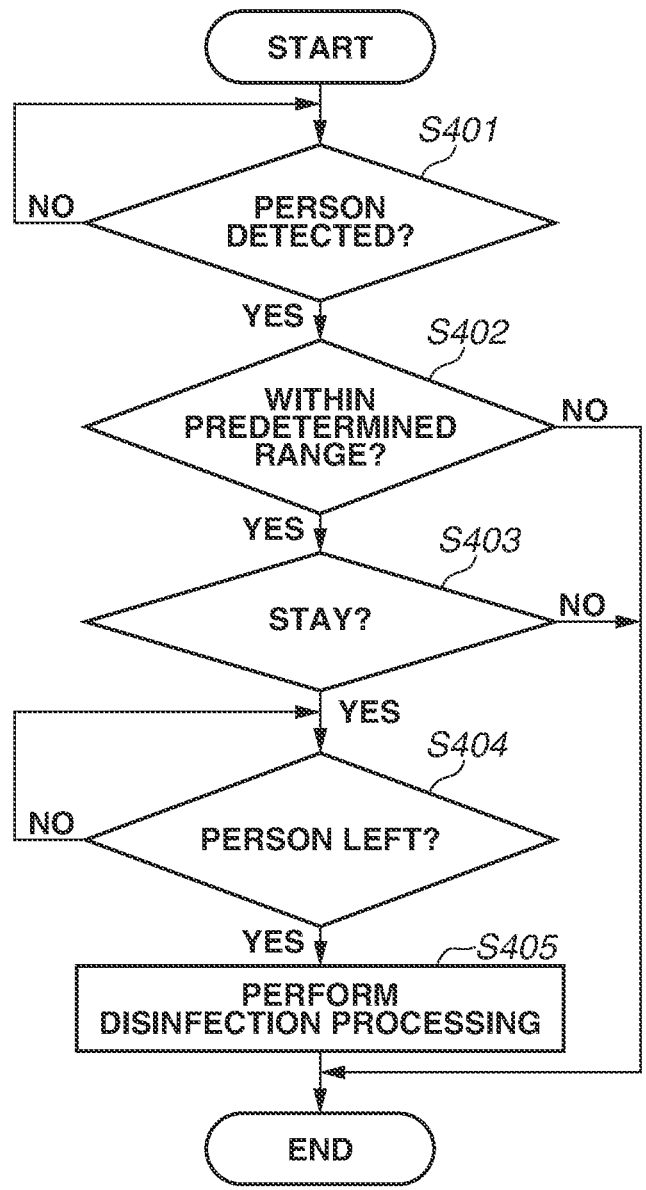
FIG. 11 is a flowchart illustrating disinfection processing.

FIG. 11 is a flowchart illustrating processing of a third exemplary embodiment.

In step S401, in a case where the CPU 301 detects presence of a person in proximity to the image formation apparatus 100 by a human presence sensor (YES in step S401), the processing proceeds to step S402, otherwise (NO in step S401) the processing remains in step S401.

In step S402, in a case where the CPU 301 determines that the person detected by the human presence sensor has approached a predetermined distance or more (YES in step S402), the processing proceeds to step S403, otherwise (NO in step S402) the processing ends.

In step S403, in a case where the CPU 301 determines that the person detected within a predetermined range stays within the predetermined range for a certain period of time (YES in step S403), the processing proceeds to step S404, otherwise (NO in step S403), the processing ends. Both the predetermined distance and the stay time can be set by the user.

In step S404, in a case where the CPU 301 detects that the person detected in step S401 is no longer within, i.e., has left, the predetermined range (YES in step S404), the processing proceeds to step S405, otherwise (NO in step S404) the processing remains in step S404. The detection of a person leaving the predetermined range means, for example, that the person is no longer in the detectable range of the human presence sensor.

In step S405, the CPU 301 controls the ultraviolet light source control unit 220 via a system bus 307 to perform the disinfection processing on the image formation apparatus 100. The disinfection processing can be performed on all units that can be disinfected, or, on only some members.

Figure 12:
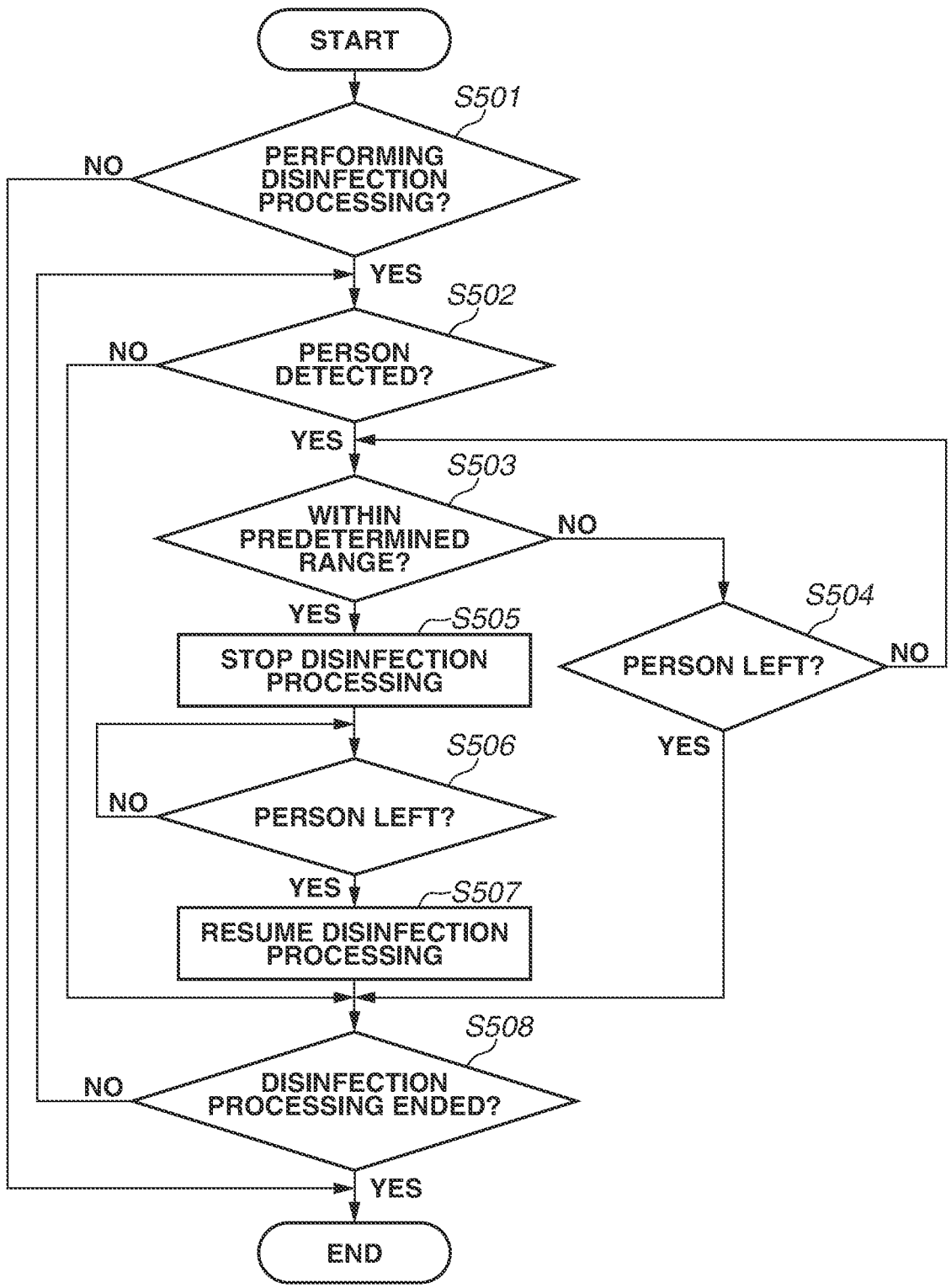
FIG. 12 is a flowchart illustrating disinfection processing.
Figure 13:
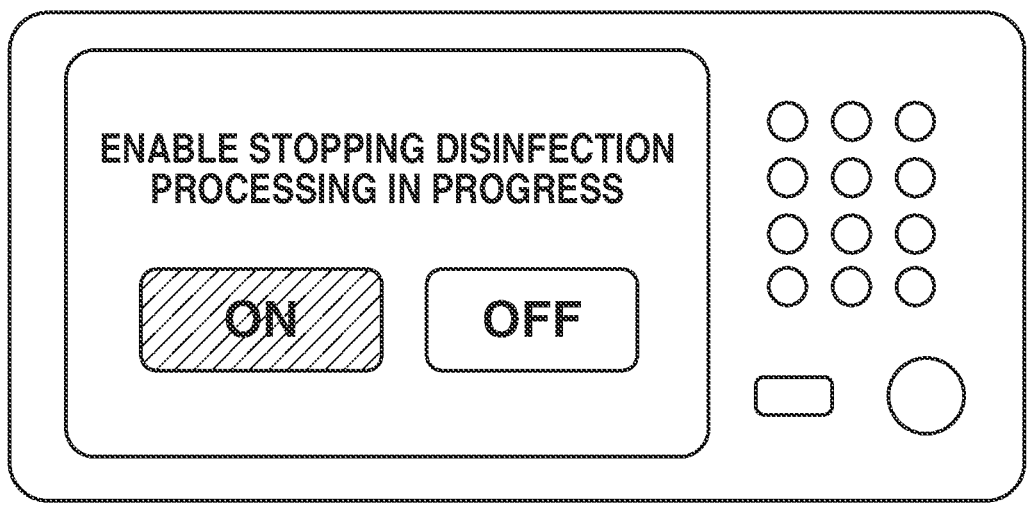
FIG. 13 is a diagram illustrating a stop setting screen for disinfection processing.

Next, a description will be provided with reference to the flowchart illustrated in FIG. 12 of a method for stopping the disinfection processing in response to detecting an approach of a person by the human presence sensor during the disinfection processing, and a stop setting screen of the disinfection processing illustrated in FIG. 13.

The setting screen of FIG. 13 is a setting screen of the image formation apparatus 100. In a case where a setting for stopping the disinfection processing in progress is enabled, after a disinfection state display is displayed, the image formation apparatus 100 stops the disinfection processing in response to detection of a person to receive an operation. According to the present exemplary embodiment, a trigger of the processing is detection of a person. In another exemplary embodiment, the trigger can be receiving a user's operation. In a case where the setting for stopping the disinfection processing in progress is disabled, after the disinfection state display is displayed, no operation is received until the disinfection processing is completed as in the first exemplary embodiment.

Turning to FIG. 12, in step S501, in a case where the disinfection processing is in progress by the image formation apparatus 100 (YES in step S501), the processing proceeds to step S502, otherwise (NO in step S501), the processing ends. The state in step S501 in which the disinfection processing is in progress by the image formation apparatus 100 corresponds to the state where the processing procedures from step S106 to step S110 in FIG. 7 are performed.

In step S502, in a case where the CPU 301 detects presence of a person in proximity of the image formation apparatus 100 by the human presence sensor (YES in step S502), the processing proceeds to step S503, otherwise (NO in step S502) the processing proceeds to step S508.

In step S503, in a case where the CPU 301 determines that the person detected by the human presence sensor approaches a predetermined range or more (YES in step S503), the processing proceeds to step S505, otherwise (NO in step S503) the processing proceeds to step S504.

In step S504, in a case where the CPU 301 detects that the person detected by the human presence sensor is no longer within the predetermined range (YES in step S504), the processing proceeds to step S508, otherwise (NO in step S504) the processing returns to step S503.

In step S505, the CPU 301 controls the ultraviolet light source control unit 220 to stop the disinfection processing.

In step S506, in a case where the CPU 301 detects that the person detected by the human presence sensor has left the predetermined range (YES in step S506), the processing proceeds to step S507, otherwise (NO in step S506) the processing remains in step S506.

In step S507, the CPU 301 controls the ultraviolet light source control unit 220 to resume the disinfection processing.

In step S508, the CPU 301 checks a count value of a timer unit 215 corresponding to a UV control unit 211 connected to the ultraviolet light source 200a-200d that has been lit. In a case where it is determined that the disinfection processing has ended (YES in step S508), the processing ends, otherwise (NO in step S508) the processing returns to step S502.

According to the configuration of the present exemplary embodiment, the user can operate the image formation apparatus 100 without waiting for completion of the disinfection processing. That is, it is possible to achieve both improved usability and a disinfection function for users who give priority to the immediate use of the image formation apparatus over the disinfection processing.

According to the configuration of the present exemplary embodiment, for example, even in a case where a wavelength of each ultraviolet light source mounted on an image formation apparatus is 230 to 290 nm, disinfection processing can be safely performed by controlling off and on of the disinfection processing in response to detection of a person's approach by a human presence sensor.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that these embodiments are not seen to be limiting. The scope of the following claims is to be accorded the broadest interpretation so as to encompass all such modifications and equivalent structures and functions.

This application claims the benefit of Japanese Patent Application No. 2020-192830, filed Nov. 19, 2020, which is hereby incorporated by reference herein in its entirety.

What is claimed is:

1. An image forming apparatus including at least one unit that receives a user operation, the image forming apparatus comprising:
an ultraviolet irradiation device configured to perform disinfection processing for disinfecting at least a part of the at least one unit;
an operation unit configured to notify a user of information;
a sensor configured to detect a presence of an object in a predetermined range from the image forming apparatus; and
a controller configured to,
control the ultraviolet irradiation device to stop the disinfection processing based on detection of the presence of the object in the predetermined range from the image forming apparatus by the sensor;
control the ultraviolet irradiation device to restart the disinfection processing based on the controller detecting that the object detected by the sensor has left the predetermined range from the image forming apparatus.

2. The image forming apparatus according to claim 1, wherein the sensor is further configured to detect whether a distance between the detected object and the image forming apparatus is within a second predetermined range, and
wherein the controller is further configured to control the ultraviolet irradiation device not to stop the disinfection processing when the sensor detects the presence of the object in the second predetermined range from the image forming apparatus in a case where the sensor does not detect the presence of the object in the predetermined range.

3. The image forming apparatus according to claim 1, wherein the controller enables an input from the user via the operation unit.

4. The image forming apparatus according to claim 1, wherein the controller is further configured to control the ultraviolet irradiation device to performs the disinfection processing in response to a lapse of a predetermined time period since the image forming apparatus last received an operational input.

5. The image forming apparatus according to claim 1, wherein the controller is further configured to set a setting for stopping the disinfection processing by the ultraviolet irradiation device.

6. The image forming apparatus according to claim 1, wherein the ultraviolet irradiation device performs the disinfection processing by irradiating the at least one unit with ultraviolet rays for a predetermined time period, wherein the predetermined time period is a time period based on an illuminance of a light source that is associated with a cumulative irradiation time of the ultraviolet irradiation device.

7. The image forming apparatus according to claim 1, wherein the operation unit includes a liquid crystal display (LCD) and a touch panel.

8. The image forming apparatus according to claim 7, wherein the at least one unit includes the operation unit, and
wherein the ultraviolet irradiation device is configured to disinfect at least the LCD of the operation unit.

9. The image forming apparatus according to claim 1, wherein the at least one unit includes a scanner unit, and
wherein the ultraviolet irradiation device is configured to disinfect at least a grip part the scanner unit.

10. The image forming apparatus according to claim 1, wherein the at least one unit includes a printer device including at least one sheet feeding cassette, and
wherein the ultraviolet irradiation device is configured to disinfect at least a grip part of the at least one sheet feeding cassette.

11. The image forming apparatus according to claim 1, wherein the controller is further configured to control the operation unit to notify the user of information indicating that the disinfection processing is in progress during the disinfection processing for the at least a part of the at least one unit by the ultraviolet irradiation device.

12. The image forming apparatus according to claim 11, wherein the controller is further configured to set a setting for stopping disinfection processing by the ultraviolet irradiation device, and
wherein, based on the setting of the stop setting, the controller enables an input from the user via the operation unit in a state where the notification that the disinfection processing is in progress is provided.

13. The image forming apparatus according to claim 11, wherein the provided notification includes a time remaining until an end of the disinfection processing.

14. The image forming apparatus according to claim 11, wherein the provided notification includes information of the part for which the disinfection processing is being performed.

15. The image forming apparatus according to claim 11, wherein the notification indicates the disinfection processing is in progress by changing a color of a button corresponding to a function performed by the image forming apparatus.

* * * * *